United States Patent [19]

Singh et al.

[11] Patent Number: 6,083,708
[45] Date of Patent: Jul. 4, 2000

[54] POLYPEPTIDE: DENDRIMER COMPLEXES

[75] Inventors: Pratap Singh, Wilmington, Del.; Spencer Lin, Granger, Ind.; Fred Moll, III, Pembroke Pines, Fla.

[73] Assignee: Dade Behring Inc., Deerfield, Ill.

[21] Appl. No.: 08/514,075

[22] Filed: Aug. 11, 1995

[51] Int. Cl.[7] .................................................. G01N 33/535
[52] U.S. Cl. .................... 435/7.92; 435/180; 435/188; 435/189; 436/518; 530/391.1
[58] Field of Search ........................... 424/1.49, 4, 78.08, 424/78.1, 9, 78.17, 78.37, 1.53, 1–69, 1.65; 436/173, 806, 518; 514/772.1, 772.3; 528/332, 310, 328, 363, 425; 435/7.92, 180, 188, 189; 530/391.1

[56] References Cited

U.S. PATENT DOCUMENTS

| | | |
|---|---|---|
| 4,363,634 | 12/1982 | Schall, Jr. . |
| 4,507,466 | 3/1985 | Tomalia et al. . |
| 4,517,288 | 5/1985 | Giegel et al. . |
| 4,568,737 | 2/1986 | Tomalia et al. . |
| 4,694,064 | 9/1987 | Tomalia et al. . |
| 5,204,448 | 4/1993 | Subramanian . |
| 5,338,532 | 8/1994 | Tomalia et al. . |
| 5,418,136 | 5/1995 | Miller et al. . |
| 5,482,830 | 1/1996 | Bogart et al. . |
| 5,541,057 | 7/1996 | Bogart et al. . |
| 5,661,025 | 8/1997 | Szoka et al. ......................... 435/172.3 |
| 5,718,915 | 2/1998 | Virtanen et al. ........................ 424/450 |

FOREIGN PATENT DOCUMENTS

| | | |
|---|---|---|
| 0 481 526 | 4/1992 | European Pat. Off. . |
| WO 82/02601 | 8/1982 | WIPO . |
| WO 88/01178 | 2/1988 | WIPO . |
| WO 90/12050 | 10/1990 | WIPO . |
| WO 91/12886 | 9/1991 | WIPO . |
| WO 93/06868 | 4/1993 | WIPO . |
| WO 94/03774 | 2/1994 | WIPO . |
| 94/19693 | 9/1994 | WIPO . |
| 95/27902 | 10/1995 | WIPO . |
| 95/28641 | 10/1995 | WIPO . |

OTHER PUBLICATIONS

Monticello et al. (Clin. Chem., vol.34, No.6, p. 1257, 1988).
Smith et al. (Clin. Chem., vol.33, No.6, p. 885, 1987).
Sheiman et al. (Clin. Chem., vol.32, No.6, p.1083, 1986).

Singh et al. "Starburst dendrimers: enhanced performance and flexibility for immunoassay". Clin. Chem., vol.40,No.9, pp. 1845–1849, 1994).

Geigel et al. "Radial Partition Immunoassay". Clin. Chem. vol.28, No.9, pp. 1894–1898, 1982.

Roberts, et al.; *Bioconjugate Chemistry*; Using Starburst Dendrimers as Linker Molecules to Radiolabel Antibodies; vol. 1, No. 5; 305–308; Sep. 1, 1990.

Singh, Pratap; *Abstracts of Papers Amer. Chem. Soc.*; Coupling of Multiple Proteins to Starburst™ Dendrimers; vol. 211, No. 1–2; p. BIOT 193; Mar. 28, 1996, New Orleans.

Abuchowski A and Davis FF, "Soluble Polymer–Enzyme Adducts," *Enzymes as Drugs*, Chapter 13, eds. Holcenberg and Roberts, John Wiley & Sons, New York, pp. 367–383.

Knauf MJ et al., "Relationship of effective molecular size to systemic clearance in rats of recombinant interleukin–2 chemically modified with water–soluble polymers," J. Biol. Chemistry 263(29): 15064–15070 (1988).

Labeque R. et al., "Enzymatic modification of plasma low density lipoproteins in rabbits: A potential treatment for hypercholesterolemia," Proc. Natl. Acad. Sci. USA 90:3476–3480 (1993).

Sherwood RF et al., "Enhanced plasma persistence of therapeutic enzymes by coupling to soluble dextran," Biochem. J. 164:461–464 (1977).

*Primary Examiner*—Donna C. Wortman
*Attorney, Agent, or Firm*—Ronald C Lundquist; Cynthia G Tymeson

[57] ABSTRACT

Compositions are disclosed, comprising dendrimers to which a first polypeptide is controllably coupled. Such polypeptide-dendrimer compositions are effective for controllably coupling a second polypeptide to the dendrimer. The first and second polypeptides have separate and distinct defined biological activities, for example, two antibodies with first and second binding specificities or an antibody and an enzymatic label. Such compositions are useful as indicators in specific binding assays, e.g., immunoassays. Methods for sequentially coupling two different polypeptides to a dendrimer to form compositions of the invention also are disclosed.

28 Claims, 1 Drawing Sheet

POLYPEPTIDE: DENDRIMER COMPLEXES

FIELD OF THE INVENTION

This invention relates generally to compositions comprising a first polypeptide coupled to a dendrimer and, optionally, a second polypeptide coupled to the same dendrimer. The invention also relates to methods for coupling a first polypeptide and, optionally, a second polypeptide to a dendrimer.

BACKGROUND OF THE INVENTION

Dendrimers are polymers of spherical or other three-dimensional shapes that have precisely defined compositions and that possess a precisely defined molecular weight. Dendrimers can be synthesized as water soluble macromolecules through appropriate selection of internal and external moieties. See U.S. Pat. Nos. 4,507,466 and 4,568,737, incorporated by reference herein. Starburst™ dendrimers are manufactured by The Dow Chemical Company.

Dendrimers have been conjugated with various pharmaceutical materials as well as with various targeting molecules that may function to direct the conjugates to selected body locations for diagnostic or therapeutic applications. See for example, WO 8801178, incorporated by reference herein. Dendrimers have been used to covalently couple synthetic porphyrins (e.g., hemes, chlorophyll) to antibody molecules as a means for increasing the specific activity of radiolabeled antibodies for tumor therapy and diagnosis. Roberts, J. C. et al., Using Starburst Dendrimers as Linker Molecules to Radiolabel Antibodies, *Bioconjug. Chemistry* 1:305–308 (1990).

It is known to directly covalently couple two different polypeptides, e.g., to form a conjugated reagent for a diagnostic assay. Polypeptide-polypeptide conjugates, although useful, have a number of disadvantages. The conjugation reaction is often relatively uncontrolled, leading to intermolecular conjugation of the two polypeptides at more sites on each polypeptide than is desired, intermolecular conjugation of two molecules of the same polypeptide, and even intramolecular conjugation within the same polypeptide molecule. The proportion of each species may vary in each production lot, resulting in variability in titer, purity, specificity and specific activity. In a solid phase diagnostic assay, certain of these species may lead to high non-specific binding and decreased assay sensitivity. Numerous and costly quality control and standardization procedures may be required when manufacturing such conjugates. Moreover, variability in the shelf life of such conjugated polypeptide reagents may be encountered due to the tendency of such conjugates to become inhomogeneously distributed within stock solutions. That is, such conjugates, while substantially soluble, may not remain completely soluble and may undergo some settling out of solution over time. Even with periodic mixing of stock solutions, gravitational influences, temperature gradients and other physical influences can cause inhomogeneities.

Dendrimer: antibody complexes have been used to form assay reagents that overcome some of the problems of polypeptide-polypeptide conjugates. The dendrimer portion of such complexes is used to facilitate immobilization of assay reagents on a solid phase. For example, antibodies have been attached to dendrimers by the formation of carbon-sulfur (C—S) linkages between a dendrimer derivatized with sulfosuccinimidyl-(4-iodoacetyl) aminobenzoate (sulfo-SIAB) and a sulfhydryl group on an antibody. See U.S. patent application Ser. No. 08/021,928, incorporated by reference herein. Known dendrimer-coupled antibodies have a very strong affinity for the glass fiber solid phase (tab) used in such immunoassays. U.S. patent application Ser. No. 08/021,928 incorporated by reference herein; U.S. patent application Ser. No. 08/226,172, incorporated by reference herein. In the spotting buffer (pH 8.0), the tab has a net negative charge whereas the dendrimer-antibody complex has a net positive charge, due to the presence of a very large number of free amino groups. The charge interaction between the dendrimer-antibody and glass fiber solid phase can be so strong as to localize the dendrimer-coupled antibody at the point of application on the solid phase.

SUMMARY OF THE INVENTION

Dendrimer/polypeptide complexes are disclosed herein. These complexes comprise a dendrimer having a plurality of termini, a first polypeptide and a second polypeptide. The first polypeptide and the second polypeptide are sequentially coupled to the dendrimer via its termini. The first and second polypeptides of the complex exhibit first and second defined biological activities, respectively. Alternatively, a dendrimer/polypeptide complex may comprise a dendrimer coupled to a first polypeptide exhibiting a first defined biological activity and at least one terminus on the dendrimer to which a second polypeptide, possessing a second defined biological activity, may be coupled. Some fraction of the termini in dendrimer/polypeptide complexes may be uncoupled. Uncoupled termini may be blocked, if desired. Dendrimers useful according to the invention include, without limitation, first, second, third, fourth, and fifth generation ethylenediamine core dendrimers. Alternatively, the dendrimer may be a first, second, third, fourth, or fifth half-generation ethylenediamine core dendrimer.

One of the defined biological activities may comprise, for example, enzymatic catalysis. Such enzymatic catalysis may comprise formation of a fluorescent, colorimetric, chemiluminescent, phosphorescent, radiometric or hybridized product after contact with a substrate. Polypeptides exhibiting such enzymatic catalysis may be, for example, alkaline phosphatase, β-galactosidase, glucose oxidase, peroxidase, urease, catalase, adenosine deaminase, glycosidase, protease, esterase, DNase, RNase and acetylcholinesterase.

Another suitable defined biological activity may comprise specific binding to an analyte or receptor for the analyte. A polypeptide having such a specific binding activity may comprise, for example, an antibody or antibody fragment having specificity for creatine kinase isozyme MB, troponin I, myoglobin, thyroid stimulating hormone, follicle stimulating hormone, luteinizing hormone or ferritin.

A method of making a polypeptide/dendrimer complex is disclosed herein. The method comprises the steps of providing a dendrimer comprising a plurality of activated termini, providing a first polypeptide having at least one reactive moiety and coupling the first polypeptide via the reactive moiety to one of the activated termini. The method forms a polypeptide/dendrimer complex that exhibits a first defined biological activity possessed by the first polypeptide. Such a complex is adapted for coupling a second polypeptide, possessing a second defined biological activity, to the dendrimer.

The dendrimer used in such a method may be a first, second, third, fourth, or fifth generation ethylenediamine core dendrimer. The reactive moiety on the polypeptide may comprise a sulfhydryl group and the activated terminus may comprise an iodoacetyl group. The dendrimer in such a method may also be a first, second, third, fourth or fifth half generation ethylenediamine core dendrimer. For such dendrimers, the reactive moiety on the polypeptide may comprise an amino group and the activated terminus may comprise an N-hydroxysuccinimidyl group.

The method may further comprise the steps of: providing a second polypeptide having at least one reactive moiety and coupling the second polypeptide via the reactive moiety to one of the activated termini to form a two polypeptide/dendrimer complex. The second polypeptide possesses a second defined biological activity and the resulting complex exhibits both the first and the second defined biological activities. For this method, both the first polypeptide and the second polypeptide reactive moieties may comprise sulfhydryl groups and the plurality of activated termini may comprise iodoacetyl, bromoacetyl, chloroacetyl, epoxy or maleimide groups.

Alternatively, when at least one of the activated termini in the first polypeptide/dendrimer complex is uncoupled, the method may further comprise the steps of activating one or more of the uncoupled termini of the complex with a second activating group, providing a second polypeptide having a reactive moiety and possessing a second defined biological activity and coupling a second polypeptide reactive moiety to a second activated terminus to form a two polypeptide/dendrimer complex. Such a complex exhibits both the first and the second defined biological activities of the first and second polypeptides, respectively. For such methods, the first polypeptide reactive moiety may comprise an amino group, the second polypeptide reactive moiety may comprise a sulfhydryl group, the plurality of activated termini may comprise N-hydroxysuccinimidyl groups and the second activated terminus may comprise a bromoacetyl iodoacetyl, chloroacetyl, epoxy or maleimidyl group.

DESCRIPTION OF THE PREFERRED EMBODIMENTS

Figure 1:
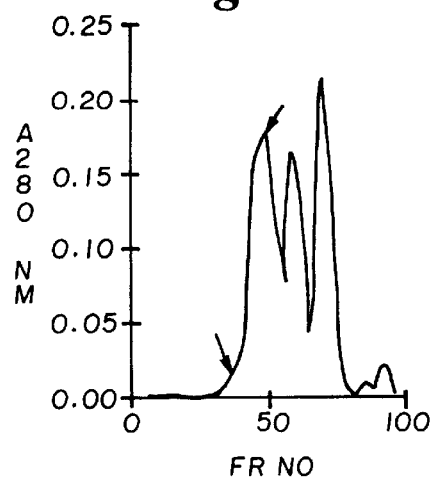
FIG. 1 shows the absorbance at 280 nanometers ($A_{280}$) of column fractions of an ALP-E1-Fab' polypeptide:dendrimer complex eluted from an Ultrogel AcA-34 column.

The applicants have made the surprising discovery that two different polypeptides, having separate and distinct biological activities, can be sequentially coupled to the same dendrimer such that the polypeptide:dendrimer ratio for each polypeptide in a composition is readily controlled and the native biological activity of each polypeptide is substantially retained.

Compositions according to the invention comprise a first polypeptide attached to at least one terminal branch of a dendrimer, which polypeptide possesses a first defined biological activity. Certain compositions may further comprise a second polypeptide, possessing a second defined biological activity and coupled to the same dendrimer.

Dendrimers useful in preparing compositions of the present invention are generally spherical branched polymers having "star" configurations as disclosed in U.S. Pat. No. 4,507,466. Star configuration dendrimers possess a structured branching wherein individual branches radiate out from a nucleus, or core region. The polyvalent core is covalently bonded to at least two ordered dendritic (tree-like) branches that extend through one or more tiers, or generations. The outermost tier or generation terminates in functional groups that may be chemically reactive with a variety of other molecules. Thus, star dendrimers are unitary molecular assemblages that possess three distinguishing architectural features, namely (a) an initiator core, (b) interior layers (generations) composed of repeating units radially attached to the initiator core, and (c) an exterior surface of activated functional groups attached to the outermost, or terminal, ends of each branch. The size, shape and reactivity of a dendrimer can be controlled by the choice of the initiator core, the number of generations employed in creating the dendrimer, and the choice of the repeating units employed at each generation. Dendrimers of discrete sizes are readily obtained as the number of generations employed increases. Generally spherical dendrimers of configurations suitable for use in the present invention are disclosed in U.S. Pat. No. 4,507,466 and U.S. Pat. No. 4,568,737, incorporated herein by reference. Alternatively, dendrimers of non-spherical configuration, such as those disclosed in U.S. Pat. No. 4,694,064, incorporated herein by reference, may be adapted for use in the present invention. Dendrimers to be used in the present invention preferably are first through fifth generation dendrimers.

Chemical modification of all or a portion of the dendrimer termini creates surface functionalities appropriate for a particular application. Dendrimers to be used in compositions according to the present invention have a functionalized group linked to one or more termini. For example, an E5 dendrimer is a fifth-generation, ethylenediamine core particle having 128 amine-terminated end (surface) groups and a molecular weight of 28,826. Similarly, an E2 dendrimer contains 16 termini, each carrying an amino group. The amine-terminated end groups impart a net positive charge to the surfaces of such dendrimers in a solution of neutral pH. As another example, a G(4½) half-generation dendrimer is a fifth generation, ethylenediamine core particle in which the carboxymethyl ester termini of the fifth generation intermediate are not converted to amino groups as the final step, but rather are converted to carboxyl groups by hydrolysis, thereby creating a molecule having 128 terminal carboxyl groups. Similarly, a G(1½)-COOH half-generation dendrimer has 16 carboxyl-terminated ends. The carboxyl-terminated end groups impart a net negative charge to the surfaces of such dendrimers in a solution of neutral pH.

Polypeptides suitable for the invention include, without limitation, antibodies, antibody fragments, binding proteins, enzymes, peptide hormones and peptides with certain repetitive sequences for specific recognition. A polypeptide to be coupled to a dendrimer may be an oligopeptide in certain embodiments. In other embodiments, a polypeptide may comprise one subunit of a multisubunit protein which, after coupling, may be suitable for interacting with remaining uncoupled subunits to reconstitute an intact, functional protein. In some embodiments, a polypeptide may have associated cofactors or metal ion ligands that are not involved in coupling to a dendrimer but are important for biological activity of the polypeptide.

In compositions according to the invention, the average number of first polypeptide molecules coupled to a dendrimer molecule (polypeptide:dendrimer ratio) may be from about 0.1 to about 10, but typically is from about 0.2 to about 2.0. It is apparent that higher generation dendrimers may have higher polypeptide:dendrimer ratios than lower generation dendrimers and, therefore, appropriate choice of dendrimer generation will assist in attaining a desired polypeptide: dendrimer ratio.

The average number of dendrimer termini that are involved in polypeptide coupling may be adjusted by varying reaction conditions, for example, reaction time, pH and the like. A dendrimer-polypeptide composition typically does not have all terminal end groups involved in polypeptide coupling. Termini that are not involved in polypeptide coupling may be converted to another form, if desired, e.g, by blocking remaining uncoupled termini with hydroxyl, alkyl, aryl, amide, nitrile, ether, thioether, or blocked sulfhydryl groups. For example, replacement of uncoupled terminal groups with uncharged terminal groups is advantageous in those cases where a net charge on the composition adversely affects the useful properties of the composition for its intended end use. Blocking of uncoupled terminal may require a separate blocking step, or may occur during the coupling step.

A first polypeptide possesses a first biological activity. Typical biological activities possessed by a polypeptide include, without limitation, specific binding to an analyte or receptor for an analyte, specific binding to cell walls or membranes, enzymatic catalysis, direct or indirect detection of a substrate, electrical charge transfer capabilities, specific dielectric constants and specific tertiary conformations that are assumed under a specified set of conditions.

A composition according to the invention may further comprise a second polypeptide coupled to a dendrimer:first polypeptide complex. If one or more second polypeptide molecules are present in a composition, the biological activity of the second polypeptide is distinct from the first polypeptide, i.e., the two polypeptides do not possess the same biological activity. However, it is recognized that in certain embodiments, both polypeptides may have the same general function but with differing specificities. For example, both polypeptides may be antibodies, each antibody recognizing separate and distinct epitopes. The two epitopes may be on the same or on a different molecule. In other embodiments, both polypeptides may be enzymes, each enzyme having a separate and distinct catalytic activity. Such embodiments are within the scope of the invention.

If a composition further comprises a second polypeptide, the polypeptide:dendrimer ratio for each polypeptide may be different, if desired, e.g., a first polypeptide may be present in a composition at a ratio of about 1:1 and a second polypeptide may be present at a ratio of about 3:1. In this case, the first polypeptide:second polypeptide ratio is about 0.33. Such ratios may be controllably varied to achieve a desired specific biological activity value per mole of dendrimer for each polypeptide.

The desired polypeptides are selected based on the end use of the dendrimer-polypeptide composition. In a preferred embodiment, one of the polypeptides is an antibody, antibody fragment, or specific binding protein and the other polypeptide is an enzyme that produces a fluorescent, calorimetric, chemiluminescent, phosphorescent, or radiometric product after contact with a substrate.

A method of controllably coupling a polypeptide to a dendrimer comprises incubating a selected generation of dendrimer containing at least one activated terminal group with a polypeptide containing at least one reactive moiety. Dendrimers useful according to the invention have at least one activated terminal group suitable for coupling a terminal group to a reactive moiety on a polypeptide. Dendrimer termini are activated by reaction of a heterobifunctional reagent with existing terminal groups. The reaction, carried out under mild conditions, does not affect characteristic structural features of the dendrimer. Controllably coupling a polypeptide to a dendrimer involves reacting an activated dendrimer terminal group with a reactive moiety on a polypeptide. Activated termini are useful for accelerating the reaction rate when coupling a polypeptide to a dendrimer. It is preferable for substantially all of the terminal groups of the dendrimer to be activated. By substantially all is meant at least 90% of the terminal groups of the dendrimer, preferably at least about 95%, more preferably at least about 99%. However, a dendrimer may have a portion of its terminal groups activated and the remainder of its terminal groups unactivated in certain embodiments.

Polypeptides typically are coupled to a dendrimer by the formation of carbon-nitrogen (C—N) linkages, carbon-oxygen (C—O) linkages, or carbon-sulfur (C—S) linkages.

Amino groups on dendrimer termini are known to be suitable for coupling to reactive carboxyl groups on polypeptides to form C—N linkages. A suitable reactive group with which to functionalize dendrimer terminal groups is an electrophilic group such as an iodoacetamido moiety. An iodoacetamido group can be introduced onto an amino terminus of a dendrimer under mild reaction conditions by treatment of an amine-containing species with an activated ester (e.g., N-hydroxysuccinimidyl esters) of a iodoacetamido-containing molecule. A number of commercial products are available for this purpose, e.g., N-hydroxysuccinimidyl iodoacetamide (NIA, available from, for example, BioAffinity Systems, Inc. Roscoe, Ill.). However, N-hydroxysuccinimidyl esters having a hydrophobic aromatic spacer group (e.g., phenyl) are not preferred, because of decreased solubility when a large number of hydrophobic groups are introduced into polypeptide:dendrimer complexes of the present invention.

A preferred group for activating carboxylated dendrimer termini is N,N,N',N'-tetramethyl (succinimido)uronium tetrafluoroborate (TSTU). This reagent converts a carboxyl group to an activated N-hydroxysuccinimidyl (NHS) ester and is preferred because it allows purification and quantitation of the NHS esterified dendrimer formed during this reaction. This activated dendrimer can be reacted directly with a polypeptide by coupling via a nucleophilic reactive moiety such as epsilon amino groups of polypeptide lysyl residues. Quantitation of an activated dendrimer intermediate allows control over the composition and purity of the final product.

As an alternative, an NHS ester of a dendrimer carboxyl terminus may be further reacted with 6-bromoacetamidohexylamine ($BrCH_2CONH(CH_2)_6NH_2$; BAHA) to incorporate an electrophilic bromoacetamido group, which forms activated dendrimer termini that may be coupled to sulfhydryl groups of a suitable polypeptide. Other dendrimer terminal functional groups that are suitable as activated termini or for converting to activated termini include maleimidyl, chloroacetyl, hydroxyl, mercapto, carboxyl, allyl, vinyl, halo, oxiranyl, aziridinyl, oxazolinyl, imidazolinyl, isocyanato and isothiocyanato. Reactive moieties on polypeptides that are suitable for coupling to activated dendrimer termini include, without limitation, sulfhydryl, amino, epoxy, iodoacetyl, aldehyde and phenyl iodoacetamido groups. Reactive moieties may comprise intrinsic functional groups present in the native polypeptide, e.g. epsilon amino groups of lysyl residues or sulfhydryl groups of cysteinyl residues. Illustrative embodiments of intrinsic groups suitable as reactive moieties are sulfhydryl groups of cysteine residues in the hinge region of an Fab' antibody fragment and E-amino groups of lysine residues in calf intestinal alkaline phosphatase.

Reactive moieties also may be introduced onto a polypeptide in a separate reaction. For example, sulfhydryl groups may be introduced by reacting a polypeptide with sulfosuccinimidyl 6-[3-(2-pyridylthio)propionamide] hexanoate (sulfo-LC-SPDP) to introduce disulfide linkages, followed by reduction of disulfide linkages with dithioethyritol (DTE). The average number of reactive moieties introduced per polypeptide may be controlled by appropriate selection of reactant ratios, incubation time, pH, temperature and the like. The actual number of reactive moieties introduced on a polypeptide may be readily determined by titration methods known in the art.

Compatible activated dendrimer terminal groups and polypeptide reactive moieties preferably are selected to allow activated termini to be coupled to reactive moieties under relatively mild reaction conditions, i.e, physiologically acceptable ranges of temperature (40°–40° C.), pH (6.0–8.5), ionic strength (0.1–0.2 M) and the like. For a polypeptide having one or more sulfhydryl groups as reactive moieties, suitable activated dendrimer termini include electrophilic groups such as epoxy, iodoacetamido or bromoacetamido groups. An appropriate polypeptide reactive moiety to use for coupling to an NHS-activated carboxyl ester dendrimer terminus is an amino group such as the epsilon amino group of a lysine residue in the polypeptide chain. Certain electrophilic groups, such as sulfosuccinimidyl-(4-iodoacetyl) aminobenzoate (sulfoSIAB) are not preferred as activated terminal groups on a dendrimer since it is difficult to functionalize substantially all of the termini under mild reaction conditions with sulfoSIAB.

Certain pairs of groups are not preferred for sequential coupling of polypeptides to dendrimers. For example, the aqueous coupling of dendrimer -COOH terminal groups to -NH$_2$ groups in a polypeptide is sometimes carried out in the presence of 1-ethyl-3-(3-dimethylaminopropyl) carbodiimide (EDC) in neutral or acidic medium. However, the EDC reagent is normally present during the reaction of activated carboxyl termini with a nucleophilic reactive moiety in this method and can produce inter- and intra-molecular linkages between the NH$_2$ groups of the polypeptide and the COOH groups of both the polypeptide and the dendrimer. The reaction products can also include undesirable cross-linked protein species. Cross-linked protein species often have less or even no biological activity per mole of protein compared to the biological activity of the native protein.

As described above, a polypeptide in a polypeptide:dendrimer complex exhibits a defined biological activity. The step of coupling a polypeptide to the dendrimer is carried out under conditions that retain such a defined biological activity in the resulting product. However, it is recognized that enhancement, reduction or elimination of other biological activities of the polypeptide may occur. Such enhancement, reduction or elimination is within the scope of the invention, provided that the defined biological activity is retained. In fact, enhancement, reduction or elimination of other biological activities may be desirable in the final polypeptide:dendrimer composition.

The ratio of a first polypeptide to dendrimer produced by a coupling reaction is readily controllable by adjusting the amounts of the two reactants, the number of reactive moieties on the polypeptide, the number of activated termini on the dendrimer and reaction conditions (time, temperature and the like). The reaction product, a first polypeptide:dendrimer complex, typically is purified upon completion of the reaction by gel filtration, e.g., Sephadex®.

The reaction product is effective for coupling a second polypeptide thereto. Effectiveness for coupling of a second polypeptide is readily achieved, by means that depend upon the chemistry of the two couplings. In those situations in which the first and second polypeptides are to be coupled to the dendrimer by similar chemistry (the same or similar reactive moieties on both the first and second polypeptide and the same or similar activated termini on the dendrimer), coupling of the first polypeptide typically will leave a number of activated terminal dendrimer groups in an activated state, i.e, not all of the activated terminal groups will be involved in coupling to the first polypeptide and will be available for coupling to the second polypeptide. Those dendrimer termini involved in coupling to the first polypeptide are, of course, no longer activated. In this situation, the reaction product of the first coupling is thereafter incubated with a second polypeptide under conditions effective for controllably coupling the second polypeptide to the first polypeptide:dendrimer complex at the desired ratio.

On the other hand, if the chemistry involved in coupling the first polypeptide is different from the chemistry involved in coupling the second polypeptide, the reaction product of the first reaction is thereafter incubated such that at least one dendrimer terminus not involved in coupling to the first polypeptide is activated with a second activation group suitable for coupling a second polypeptide to the dendrimer:first polypeptide complex.

Reaction conditions for coupling a second polypeptide are controlled in a manner similar that described above for the first coupling reaction, such that a desired average number of second polypeptide molecules are coupled to a dendrimer molecule.

The average number of polypeptide molecules per dendrimer will depend to some extent upon the dendrimer generation selected, since higher generation dendrimers support coupling of more polypeptides. Typical polypeptide/dendrimer ratios are from about 0.1 to about 2 molecules per dendrimer. The end use of a particular polypeptide: dendrimer complex affects the desired ratio in two polypeptide:dendrimer complexes. For example, if a complex comprises a label polypeptide and a specific binding polypeptide and is to be used as an indicator or specific competitive reagent in a specific binding assay, it may be desirable to have a relatively larger number of label polypeptides per dendrimer compared to the number of specific binding polypeptides per dendrimer.

Polypeptide:dendrimer complexes may, and often do, have residual dendrimer termini that are not involved in polypeptide coupling. Such termini may have properties that are undesirable in the final product, e.g., may be charged at physiological pH. If desired, such uncoupled terminal groups may be converted to or replaced with a more desirable terminal group, e.g., an uncharged group, which conversion or replacement may be termed "blocking". However, it is recognized that blocking is not necessary for many end uses and that the presence of uncoupled terminal groups may even be desirable for some end uses.

Polypeptide:dendrimer complexes according to the invention present a number of distinct advantages. First, dendrimers are produced with precise polymer chemistries and can be designed to have a precise number of generations yielding a precise molecular size, weight and surface composition. Because of the uniform and well-characterized chemistry, such parameters remain uniform over different manufacturing lots. The uniformity in dendrimer properties leads to uniformity in polypeptide:dendrimer compositions compared to directly coupled polypeptide-polypeptide conjugates. Second, dendrimers having appropriate interior and surface compositions can be manufactured to be water soluble, such that dendrimer:polypeptide complexes are more likely to remain in solution and maintain solution homogeneity over time. Third, sequential coupling of two different polypeptides to a dendrimer has been discovered to avoid the variations and limitations of simultaneous coupling of polypeptides to a dendrimer.

Polypeptides incorporated into compositions according to the invention surprisingly retain the defined biological activity present in the unincorporated native polypeptide. Compositions having a second polypeptide exhibit the defined biological activity of both the first and the second polypeptides, regardless of the similarity or dissimilarity between the two coupling chemistries. Although the present invention is not bound by theory, it is believed that factors such as steric inhibition and undesired coupling to active site polypeptide residues do not occur, contrary to expectations.

Sequential coupling of polypeptides to a dendrimer allows control over the complex formed regardless of the relative reactivities of the polypeptides, even when the same chemistry is utilized for both coupling reactions. In contrast, successful simultaneous coupling requires the first and second polypeptides to have the same or similar reactivities with the dendrimer/activated dendrimer; if the first and second polypeptides have different reactivities, the more reactive polypeptide will preferentially react with the dendrimer. For example, it was found that all efforts to simultaneously couple alkaline phosphatase (ALP) and an antibody to a dendrimer gave a product in which only ALP was coupled to the dendrimer. Thus, simultaneous coupling of two polypeptide species requires two very similar reactivities which is very difficult to achieve. Alternatively, the reactivity of one of the two polypeptide species can be modified prior to simultaneous coupling which, however, can cause a loss in biological activity.

Dendrimer:two-polypeptide compositions are useful as industrial bioreactors, as biological standards, or as affinity chromatography media. Many biological systems and enzyme reactors depend on sequential reactions catalyzed by different enzymes. In these reactions, the product of one enzyme-catalyzed reaction is the substrate for the other enzyme. These coupled reactions have found broad applications in a number of processes, including commercial chemical production as well as analytical purposes. A few examples are: the conversion of sucrose to fructose by a combination of invertase-glucose isomerase, conversion of D-amino acids to $\alpha$-keto acids by a combination of D-amino acid oxidase-catalase, quantitation of tryptophan by a combination of tryptophanase-lactate dehydrogenase and microassay of L-aspartate by the combination of aspartate aminotransferase-malate dehydrogenase. Dendrimer:two-polypeptide complexes are especially suited for these kinds of applications either in homogeneous solution or separated from the reaction mixture in a hollow fiber reactor or immobilized on a solid surface.

Dendrimer:two-polypeptide compositions are useful in chromatographic procedures requiring purification of two or more chemical species by differences in their properties. Thus, a separation of two species, either from each other or from a complex mixture, can be carried out by attachment of first and second antibodies to a dendrimer, each antibody having a different pH dissociation curve. In this procedure the first species can be dissociated from its antigen-antibody complex at a first pH, e.g. 6.0, whereas the second species can be dissociated at a second pH. Alternatively, this process can be carried out by addition of dendrimer:two-polypeptide complex to a mixture of the two species followed by separation of a first antigen-antibody complex by ultrafiltration. Alternatively, the dendrimer:two-polypeptide complex can be separated from a mixed solution by using an appropriate size membrane.

A preferred use for a polypeptide:dendrimer complex is as an indicator in a specific binding assay, i.e., assays that utilize specific receptors to distinguish and quantify analytes. In such assays, an analyte must be distinguished from other components found in a sample, which is accomplished by reacting the analyte with an indicator containing a specific receptor for that analyte and a label. The amount of indicator present is determined by detecting the amount of label present and correlating this amount to the concentration of analyte. The term "indicator" in the context of this invention comprises a dendrimer coupled to a specific receptor polypeptide and a label polypeptide.

A polypeptide receptor, e.g., an antibody, antibody fragment, or other specific binding protein (such as Intrinsic Factor or Folate Binding Protein), of an indicator is characterized by having a reversible specific binding affinity for an analyte or an analogue of that analyte. As used herein, an analogue generally is an analyte derivative carrying a marker suitable for direct or indirect detection. The analogue is capable of binding to a receptor with about the same specificity and affinity as the analyte.

A label of an indicator comprises a polypeptide suitable for direct or indirect detection of the amount of indicator present, preferably in a quantitative manner. A label may be, for example, an enzyme producing a fluorescent, colorimetric, chemiluminescent, phosphorescent, radiometric or hybridized product after contact with a substrate. Illustrative examples of enzymatic labels include alkaline phosphatase, $\beta$-galactosidase, glucose oxidase, peroxidase (such as horseradish peroxidase), urease, catalase, adenosine deaminase, glycosidase, protease, esterase, DNase, RNase and acetylcholinesterase.

Dendrimer:two-polypeptide complexes are useful as indicators in immunoassays such as those using glass fiber filters as a solid phase. Giegel et al., Clin. Chem. 28:1894–98 (1982) and in U.S. Pat. No. 4,517,288, incorporated by reference herein. It is desirable to minimize non-specific binding of indicators onto a solid phase such as glass fiber. Dendrimer:two-polypeptide indicators of the invention advantageously have very low levels of non-specific binding.

The dendrimer-polypeptide complexes of the present invention are applicable to a variety of specific binding assay formats. For example, various direct-binding assays may be employed with these reagents. In such assays, receptors such as antibodies or binding proteins are immobilized on a solid phase. The immobilized receptor complexes are contacted with a sample containing the analyte of interest. Following binding of the analyte by the immobilized receptor, the solid phase is washed and then contacted with a dendrimer:two-polypeptide indicator, one of the polypeptides having affinity for the analyte and the other polypeptide functioning as a label. The extent to which the indicator is present on the solid support can be correlated with the amount of unknown analyte as disclosed, for example, in Tijssen, P., *Laboratory Techniques in Biochemistry and Molecular Biology*, Practice and Theory of Enzyme Immunoassay, pp. 173–219 (Chapter 10) and pp. 329–384 (Chapter 14), Elsevier Science Publishers, Amsterdam, The Netherlands, 1985.

Dendrimer:two-polypeptide complexes also may be used as specific competitive reagents in competitive assay formats. In such formats the solid phase, containing immobilized receptor or other molecule with specificity for a selected analyte, is contacted with a sample presumably containing such an analyte and with a specific competitive reagent. The specific competitive reagent comprises a dendrimer coupled to a polypeptide analogue of the analyte and a polypeptide functioning as a label. In this embodiment, the analogue competes with the sample analyte for binding to the receptor immobilized on the solid phase.

In an alternative embodiment, analyte may be coupled to a solid phase and contacted with a sample and with a specific competitive reagent, comprising a dendrimer coupled to a polypeptide functioning as a specific receptor for the analyte and to a polypeptide functioning as a label. In this format, sample analyte competes with solid phase analyte for binding of the soluble receptor. In both embodiments, the amount of polypeptide label bound to the solid phase after washing provides an indication of the levels of analyte in the sample. That is, the amount of label bound to the solid phase is inversely proportional to the amount of analyte in the sample.

Radial partition immunoassay as disclosed in Giegel et al., Clin. Chem. 28:1894–98 (1982) and in U.S. Pat. No. 4,517,288, incorporated herein by reference, is an assay procedure in which all steps are conducted directly on a solid phase. Antibodies or other receptor reagents are immobilized on a small area of glass fiber filter paper. Various calibrators containing known amounts of an analyte to be detected or various unknown samples potentially containing such an analyte are then incubated with this immobilized receptor. Following appropriate additions of indicators or other labeling reagents, excess reagents are removed from the center area of the filter paper by application of a wash fluid. In the case of an enzyme immunoassay, the wash fluid may contain the substrate for the enzyme, thus initiating the enzyme reaction simultaneously with the wash step. Preferably the action of the enzyme on the substrate generates a fluorescent signal. The enzyme activity in a part of the center area is then quantifiable by front-surface fluorometry. Depending on the assay format, i.e., direct binding assay or competitive assay, the rate of fluorescence is directly or inversely proportional to the concentration of analyte in the sample. Dendrimer:two-polypeptide complexes may be used as indicators in radial partition immunoassays.

Alternatively, dendrimer:two-polypeptide compositions disclosed herein may be used as indicators in "pre-mix" specific binding assays as disclosed in U.S. patent application Ser. No. 08/227,364, incorporated herein by reference.

Various instruments are available for applying dendrimer:two-polypeptide indicators or specific competitive reagents, as well as various other binding assay reagents to a solid phase, washing the solid phase, and reading the amount of indicator or competitive reagent bound to the solid phase. In a preferred embodiment, the solid phase comprises glass fiber filter tabs and the instrument comprises a Stratus® or Stratus® II Immunoassay System, available from Dade Diagnostics Inc. This instrument is a batch-processing bench-top instrument, adapted to process tabs in the radial partition immunoassay format. Giegel et al., Clin. Chem. 28:1894–98 (1982). The instrument includes fluid dispensers for sample, conjugate and substrate washes. Microprocessor-controlled stepping motors aspirate and dispense required aliquots of reagents. All timing and operational aspects of the dispensers are predetermined by a program routine within the analyzer. The instrument also includes a tab transport system, heated platens with temperature monitoring, sample and reagent fluid pumps, a read station, data processing, and means for tab disposal. For quality control, the instrument microprocessor control program periodically verifies critical operating conditions such as reference voltages, temperatures, and dispensing settings, and flags for out-of-limit values.

The polypeptide-dendrimer complexes of the invention can be used in analytical protocols for a variety of biological materials. For example, dendrimer:polypeptide complexes may be useful for immunoassay of blood or urine for the presence of therapeutic drugs, natural or synthetic steroids, hormones, enzymes or antibodies.

Other analytes that can be quantitated in such protocols include, without limitation, digoxin, dilantin, phenobarbital, theophylline, gentamicin, quinidine, and the like. Dendrimer-polypeptide complexes prepared in the foregoing manner can also be used as indicators or specific competitive reagents for the detection of steroids such as cortisol, aldosterone, testosterone, progesterone, and estriol or serum protein such as ferritin. Hormone levels are also capable of determination through the use of dendrimer-polypeptide indicators or specific competitive reagents of the present invention. These hormones include, without limitation, thyroid hormones such as tetraiodo-and triiodo-thyronine and thyroid stimulating hormone (TSH); peptide hormones such as insulin, corticotropin, gastrin, angiotensin, and proangiotensin; and polypeptide hormones such as thyrotropin, levetotropin, somatotropin and human chorionic gonadotropic hormone (HCG).

Other applications of the complexes of the present invention include assay of relatively small molecules involved in metabolism, e.g., folate, to assay polypeptide antigens and antibodies associated with infectious disease, e.g., antigens and antibodies associated with HIV, hepatitis, CMV, syphilis, Lyme disease agents, and numerous other infectious agents. Other applications include assay of compounds associated with cardiac testing, e.g., creatine kinase isozyme MB (CKMB), troponin, myoglobin, carbonic anhydrase 3 and digoxin and compounds associated with cancer diagnosis, e.g., carcinoembryonic antigen (CEA), alpha-fetoprotein (AFP) and human chorionic gonadotropin hormone (HCG).

Polypeptide-dendrimer compositions according to the invention are less expensively and more rapidly prepared than directly coupled protein-protein conjugates, or simultaneously coupled two polypeptide:dendrimer complexes, since there is less need for extensive quality control and standardization procedures. The ratio of first polypeptide:dendrimer in compositions according to the invention may be readily controlled, as can the ratio of second polypeptide:dendrimer in compositions containing a second polypeptide.

Other advantages include the fact that less protein is required to achieve a given sensitivity of an indicator, compared to directly coupled polypeptide-polypeptide conjugates. In some cases, 25% less polypeptide is required. The higher specific biological activity is at least partially a result of the controllable, sequential coupling that is achieved by the present invention.

Another advantage is that indicators and specific competitive reagents of the present invention may be used to achieve signal amplification not achievable with directly coupled polypeptide-polypeptide conjugates or simultaneously coupled polypeptide:dendrimer complexes. This is done by controllably coupling a relatively larger number of polypeptide label molecules per dendrimer and a relatively smaller number of specific binding polypeptide molecules per dendrimer. Such controlled coupling and signal amplification is difficult to achieve with other polypeptide-polypeptide indicators.

The invention will be further understood with reference to the following illustrative embodiments, which are purely exemplary, and should not be taken as limiting the true scope of the present invention as described in the claims.

EXAMPLE 1

Phenyl iodoacetamido- and sulfhydryl-activated dendrimers.

Experiments were carried out to activate ethylenediamine dendrimers from generations 1 through 5 (E1–E5) by incorporating phenyl iodoacetamido groups onto amino terminal groups of the dendrimer. A limited number of phenyl iodoacetamido groups were incorporated by adding one-fifth volume of 0.5 M sodium phosphate buffer, pH 7.0 to an aqueous solution containing approximately 2% dendrimer by weight (Michigan Molecular Institute, Midland, Mich.). The pH of the solution was adjusted to 7.6. A freshly prepared solution of 20 mg/ml sulfo-SIAB (Pierce Chemical) was added with constant mixing to the dendrimer solution at about a 10: to 25:1 molar ratio (sulfo-SIAB:dendrimer). The mixture was incubated at 30° C. for one hour and then loaded onto a Sephadex® G-25 column prepared and eluted with 0.1 M sodium acetate, pH 4.5. The first peak eluted from the column, as detected by absorption at 280 nm, contained the derivatized dendrimers. It was collected and either stored in an ice bath for no more than 12 hours prior to its use or stored frozen at –10° C. for up to two weeks. To incorporate the maximum possible number of phenyl iodoacetamido groups, a 2.5% methanolic solution of E2 (23.4 mM) was mixed slowly with a solution of SIAB in THF-methanol (234 mM; Pierce Chemical Co.). After ten minutes at ambient temperature, a white solid precipitated out from an initially clear solution. Once isolated, this precipitate was found to be insoluble in all common solvents, such as alcohol, dimethylsulfoxide (DMSO) or dimethylformamide (DMF) and buffers of pH 2.0 to 11.0. A suspension of material showed a positive color reaction for amino groups as tested with TNBS at room temperature by a procedure similar to that described by L. U. Obi 'Application of the 2,4,6-trinitrobenzene-1-sulfonic acid (TNBS) method for determination of available lysine in maize seed' Agric. Biol. Chem.: 46, pp 15–20 (1982).

Fifth-generation dendrimer, E5, was reacted with Sulfo-LC-SPDP (Sulfosuccinimidyl 6-[3-[2-pyridyldithio] propionamide]hexanoate), from Pierce Chemical Company, Rockford, Ill. in aqueous methanol at ambient temperature for 1 hour. A 8:1 molar ratio of the activated reagent:dendrimer was used for this reaction. About 4.0 protected sulfhydryls/dendrimer were incorporated at terminal groups to form protected E5-SH. The product (E5-S-S-Py) was reacted with gluconolactone, butyrolactone or acetoxyacetyl chloride in an attempt to convert the remaining amino groups in E5-S-S-Py to hydroxyl groups. Analysis of the reaction products indicated that complete conversion of the remaining amino groups to hydroxyl groups in SPDP-treated E5 was not attained with such reagents.

SPDP-treated E5 was carboxylated with succinic anhydride to form succinylated-E5-S-S-Py. The reactions were carried out by treating the methanolic solution of E5-S-S-Py with an excess of succinic anhydride solution in THF at ambient temperature. Completion of the reaction was monitored by the absence of a color reaction with TNBS which detects the presence of free primary amino groups. Analysis of the reaction product indicated that remaining amino groups in E5-S-S-Py were essentially replaced by a carboxyl group. The protected moieties on the sulfhydryl groups of succinylated-E5-S-S-Py were then removed using dithioerythritol (DTE). The resulting product, succinylated-E5-SH was found to form an insoluble precipitate on storage at –20° C.

EXAMPLE 2

Linking of Reactive Moiety to Polypeptides

An antibody directed against creatine kinase isozyme MB (CKMB, Conan, ATCC Accession No. HB8939, molecular weight about 150,000) was purified over an Affi-Prep Protein A column (BioRad) by eluting the adsorbed protein using 100 mM phosphate, pH 6.0, containing 5 mM EDTA.

The anti-CKMB antibody was digested at 37° C. with 2% pepsin for 24 hours at pH 4.2 to produce the fragment F(ab')$_2$ with a molecular weight of 100,000. The anti-CKMB F(ab')$_2$ at 3.2 mg/ml in 100 mM phosphate, pH7.0 was mixed with sulfoSIAB (in water) at a 25-fold molar excess of sulfoSIAB and incubated at 30° C. for 1 hour. The resulting SIAB-activated F(ab')$_2$ was purified by gel filtration on Sephadex® G-25 and was determined to contain 0.6 reactive phenyl iodoacetamido moieties/polypeptide.

Calf intestinal alkaline phosphatase (referred to herein as ALP) was reacted at 2.6 mg/mL in 100 mM phosphate buffer, pH 7.6 at a 20-fold molar excess of Sulfo-SIAB in essentially the same manner as described above for F(ab')$_2$. After purification, sulfoSIAB-activated ALP was found to contain 4.6 reactive phenyl iodoacetamido moieties/polypeptide.

EXAMPLE 3

Sequential Coupling of SIAB-polypeptides to SH-dendrimers

Succinylated-E5-SH from Example 1 was reacted with SIAB-activated F(ab')$_2$ from Example 2 at pH 6.0, 4° C. for 20 hours in 100 mM phosphate buffer containing 5 mM EDTA buffer. The product was purified by gel filtration on Sephadex G-25. Purified F(ab')$_2$-succE5-SH was reacted with the SIAB-activated ALP of Example 2 at pH 7.60, 4° C. for 94 hours. The resulting product was purified by gel filtration on AcA-34, yielding ALP-succE5-F(ab')$_2$. The molecular weight of the product was calculated to be 706,860. The molecular weight of the product is more than twice that of an ALP-Fab' indicator prepared by direct conjugation using SIAB (ALP-SIAB-Fab').

The ALP-succE5-F(ab')$_2$ product was used as an indicator in a CKMB assay as described in U.S. patent application Ser. No. 08/021,928, incorporated by reference herein. The assay was performed on a Stratus® II instrument by aspirating and delivering about 60 μl of a selected calibrator onto a glass fiber tab. About 20 μl of ALP-succE5-F(ab')$_2$ (167 ng protein/ml) were then delivered to each tab. The instrument then aspirated about 70 μl of substrate wash (pH 9.0 Diethanolamine buffer containing 1.0 mM 4-methylumbelliferyl phosphate (MUP), alkaline phosphatase inhibitor, stabilizers, blue dye, surfactant and 0.1% sodium azide) and released 20 µl and 50 µl sequentially to each tab. As soon as the second substrate wash was delivered, the initial fluorescence rates were measured and recorded in instrument memory. The amount of fluorescence generated by action of ALP on the MUP substrate was detected by the instrument and converted to a "rate" expressed in voltage per unit time, which is presented in the Tables and Figures as mV/min. The rate is a measure of the intensity of the fluorescence, which is, in turn, a measure of the amount of polypeptide:dendrimer complex bound to the reactive portion of the tab.

If an unknown sample is being measured during an instrument run, the fluorescence rates of individual calibrators are measured and the values directed to storage locations in a microprocessor memory. After all calibrators have been measured, the program calculates "Rodbard" parameters A, B, C and D using a multi-pass linear regression routine that fits a mathematical relationship to the measured data points in the form shown in the following equation:

$$R=\{(A-D/[1+B(X/C)]+D\}$$

where R is the fluorescence rate and X is the corresponding concentration. The equation is a generalized sigmoidal curve that has been reported to give an excellent fit in various immunoassay systems. Based on the resulting A, B, C and D parameters stored in memory, the instrument provides a concentration readout for the samples assayed.

For this experiment, calibrators A, B and F were prepared in a Tris-buffered solution (pH 7.5) including BSA, stabilizer and 0.1% sodium azide as a preservative. Calibrator solutions A, B and F contained concentrations of 0.0, 3.9 and 131.6 ng of CKMB/ml, respectively.

The results of the experiment are shown in Table 1. Similar results were obtained in two additional experiments.

TABLE 1

| Fluorescence Response of ALP-SuccE5-F(ab')₂ | | | |
|---|---|---|---|
| Calibrator | A | B | F |
| Response (MV/min)[a] | 698 | 872 | 3898 |

[a]500 ng of polypeptide/ml of indicator solution.

EXAMPLE 4

Epoxide- and SIAB-Dendrimers

A carboxymethylated-E5 dendrimer (CME5) was prepared by treatment of E5 with an 108 fold excess of bromoacetic acid in methanol solution at 37° C. Partially (77%) hydroxylated-E5 (77%E5) was made by using an ethylenediamine/ethanolamine mixture in the final reaction step to form the fifth generation termini. (Michigan Molecular Institute, Midland, Mich.).

Dendrimers E5, E2, 77%E5 and succinylated-E5 were reacted with epibromohydrin in the presence of a base such as triethylamine or suspended solid sodium carbonate for 16 hours at ambient temperature in 50% ethanol. The dendrimer reaction products contained termini with epoxide groups derived from the epibromohydrin reactant. Epoxide-activated dendrimer derivatives were completely soluble in 50% alcohol.

The number of epoxy groups incorporated into the dendrimer reaction products was quantitated by a titration procedure similar to that described in Ngo, T., ed., *Nonisotopic Immunossay*, Plenum Press, New York (1988), p. 37. The titration was performed by incubating a known volume (0.9 mL) of the activated-dendrimer solution with 0.1 mL of 0.5 mM DTE at pH 6.0 for 2.5 hours at 37° C. The amount of excess DTE that remained in the reaction mixture was quantitated by addition of 40 µL of a 5 mM aqueous alcoholic solution of dithiodipyridine (Aldrich Chemical Co.) and measuring absorption at 324 nm. The amount of DTE consumed during this reaction is equivalent to the concentration of the active groups present on the activated-dendrimer. The titration results indicated that 95–99% of the terminal amino groups on each dendrimer had been linked to an epoxy reactive group after treatment with epibromohydrin.

Carboxymethylated-E5 and 77% hydroxylated-E5 were each treated at pH 7.4 with sulfoSIAB at molar ratios of 12:1 and 8:1, respectively, of dendrimer:sulfoSIAB. These challenge ratios allowed the retention of a small number of free amino groups on each dendrimer derivative.

EXAMPLE 5

Sequential Coupling of SH- and CHO-Polypeptides to Epoxy- and SIAB-Dendrimers

An Fab' fragment of anti-CKMB antibody (molecular weight about 46,000, herein termed Fab') was prepared by DTE treatment of F(ab')₂ (Example 2) at pH 6.0 for 1 hour at 37° C. in 100 mM phosphate buffer. The sulfhydryl moiety in the hinge region of the Fab' was utilized as a reactive moiety to couple the polypeptide to dendrimers.

ALP was treated with sodium periodate to introduce reactive aldehyde moieties on the carbohydrate groups of ALP to form ALP-CHO. This reaction was carried out by a procedure similar to that described in Bioconj. Chem.:5, pp. 482–490 (1994).

ALP also was treated with Sulfo-LC-SPDP by a procedure identical to that described for activation of ALP by sulfo-SIAB (Example 2); the reaction product then was reduced at ambient temperature by adding 1 part 100 mM DTE, pH 7.6, to 9 parts reaction product and incubating for 30 minutes. The resulting polypeptide product (ALP-SH) contained about 4.5 sulfhydryl reactive moieties linked to reactive amino groups of lysyl residues in ALP. Three separate reactions then were carried out in which Fab' and the ALP derivatives were sequentially coupled to derivatives of E5. In reaction 1, Fab' was reacted with epoxy-activated E5 (Example 4) by concentrating a reaction mixture, containing 12 mg Fab' and 10 mg activated-E5 in 100 mM phosphate, pH 6.5, such that the protein concentration in the incubation mixture was at about 5.0 mg/mL. After incubation at 4° C. for 23 hours, the pH of the reaction mixture was adjusted to 7.67 and incubation continued for an additional 17 hours at 4° C. The resulting first polypeptide:dendrimer complex was purified by gel filtration over a AcA-44 column and found to contain about 3.1 uncoupled epoxide-activated termini. Purified Fab'-E5-epoxide (3.9 mg) then was added to a solution of ALP-SH (3.0 mg). The reaction mixture, in 100 mM phosphate, pH 7.6, was concentrated to a total protein concentration of about 5.0 mg/mL and then incubated at 4° C for 63 hours. Excess free sulfhydryls were quenched by the addition of 10 µL N-ethylmaleimide (10 mg/mL in DMF) for each mL of the reaction mixture.

In reaction 2, Fab' (3.2 mg) was reacted with SIAB-activated carboxymethylated-E5 (termed CME5-SIAB, 14 mg; Example 4) in 100 mM phosphate, pH 6.0. After incubation at 4° C. for 24 hours, the resulting first polypeptide-dendrimer complex was purified by gel filtration over a Sephadex® G-25 column and found to contain about 16 unconjugated SIAB-activated termini. Purified Fab'-E5 ($CH_2COOH$)-$NHCOPhNHCOCH_2I$ complex (2.2 mg) was then added to a solution of ALP-SH (3.1 mg) and incubation carried out at pH 7.6 as described above in reaction 1.

In reaction 3, the order of coupling of the two polypeptides to dendrimer was reversed. ALP-CHO was coupled by concentration of a solution containing 8.1 mg ALP-CHO and 15.9 mg SIAB-activated CME5 in 100 mM phosphate, pH 7.6. The reaction mixture (1.2 mL, containing abut 5.0 mg/mL protein) was incubated at 4° C. for 16 hours. The pH was adjusted to pH 6.30 and the mixture combined with 200 μL of sodium cyanoborohydride (30 mg/mL in water). After one hour at ambient temperature, the reaction mixture containing ALP:dendrimer complex was purified by gel filtration over Sephadex G-25 in 100 mM phosphate, pH 7.6. Purified ALP-E5($CH_2COOH$)-$NHCOPhNHCOCH_2I$ complex (4.7 mg) was then added to a solution of Fab' (2.3 mg) and incubated for 24 hours as described above in reaction 1.

The three dendrimer:polypeptide reaction products were each passed over an AcA-34 column and the $A_{280}$ of pertinent fractions was measured. The column profiles showed the presence of species with molecular weights of about 300,000, demonstrating that an ALP-E5-Fab' complex was formed in all three reactions.

The product of reaction 1 was used as an indicator in a Stratus® CKMB assay as described in Example 3. The product had fluorescence rates of 4364 and 4899 mV/min for calibrators A and F, respectively. Similar results were obtained for the products of the other two reactions.

EXAMPLE 6

Coupling of ALP to SIAB-, Epoxy-and Iodoacetyl-Dendrimers

ALP-77%E5-$NHCOPhNHCOCH_2I$, containing about 15.3 SIAB-activated uncoupled termini, was prepared by coupling ALP-CHO with SIAB-activated 77% E5 using the conditions described for Reaction 3 (Example 5) and purified by gel filtration over Sephadex® G-25. About 20 μl of the product was used as an indicator (at 0.94 ng protein/ml indicator) in a Stratus® CKMB assay as described in Example 3. The fluorescence response was 2028 mV/min on a paper tab containing no calibrator or sample (blank paper tab).

Dendrimer E2 was activated with epibromohydrin as described in Example 4. E2 also was activated with N-hydroxysuccinimidyl iodoacetate (NIA) (BioAffinity Systems, Roscoe, Ill.). A solution of NIA in alcohol-THF (1:1) was added slowly to a 50% alcoholic solution of E2, containing 1% w/v E2 dendrimer and incubated at ambient temperature for 1 hour. In this reaction, the dendrimer was activated with a twenty fold molar excess of NIA. The resulting iodoacetyl-activated dendrimer was obtained as a yellow resin on evaporation of the solution under reduced pressure. The product was dissolved in a 1:1 mixture of alcohol and 100 mM phosphate, pH 7.2 and used immediately. Essentially all dendrimer termini were activated in these procedures. The two activated E2 derivatives, containing electrophilic epoxy or iodoacetamido termini, were each coupled to ALP-SH (containing 2.6 free sulfhydryls per polypeptide molecule) as described in Example 5.

Each ALP-dendrimer complex was used as an indicator in a Stratus® CKMB assay on a blank paper tab as described above. The fluorescence response using ALP-E2-$COCH_2I$ was about 1058 mV/min at 100 ng protein/ml indicator. The fluorescence response of ALP-E2-epoxide was calculated to be about 50,130 mV/min at 100 ng protein/ml indicator.

The ALP-E2-$COCH_2I$ complex was incubated with 1/5 volume of 100 mM aminoethanethiol in 100 mM phosphate buffer, pH 7.2 for 16 hours. Aminoethanethiol reacts with the reactive iodoacetyls present in the dendrimer-polypeptide complex and introduces an amino group in place of each iodoacetyl. The aminoethanethiol-treated complex was then used as an indicator in a Stratus® CKMB assay with blank paper tabs as described above. The fluorescence response using the aminoethanethiol-treated complex as indicator was about four-fold higher than the response using untreated complex.

EXAMPLE 7

Coupling of ALP-SH to Iodoacetyl-Dendrimers

Sulfhydryl reactive moieties were linked to ALP as described in Example 5, except that a 10-fold excess of Sulfo-LC-SPDP at pH 7.0 was used. The ALP-SH product contained one free sulfhydryl per mole of protein.

NIA was used to activate the amino termini of various E1–E5 dendrimers with iodoacetyl groups. To a 50% alcoholic solution of dendrimer (1–3%, w/v) a THF solution of NIA, containing 10–25% excess of the activating reagent, was added dropwise. Thus, for example, E1 and E3 containing 8 and 32 terminal groups, respectively, were reacted with 10:1 and 35:1 molar ratios of NIA:dendrimer. After reaction for one hour at ambient temperature, most of the volatile reagents were removed on a rotary evaporator at a bath temperature of <25° C. The residual aqueous solution/suspension was diluted with an equal volume of alcohol. The aqueous alcoholic, slightly turbid, solution of NIA-activated dendrimer was stored at 4° C. until used, normally within 4 hours of preparation.

Fluorescamine titration (Lai, C.Y., Methods Enzymol. 47:236–243, 1977) of NIA-activated dendrimers indicated that none of the primary amino groups originally present could be detected. This observation suggested that >99% of all the primary amino termini had been converted to NHS-activated termini by this reaction. The number of NIA-activated termini in E1 (IAEL) was not determined due to the lability of the group.

ALP-SH was coupled to NIA-activated E1 by incubating 1.0±0.1 mg/ml of the ALP-SH product described above (12.0 ml, 85 gM; 100 mM phosphate, pH 7.0) with about 0.1 volume of 50% alcoholic solution of IAEI (1.5 ml; 20 mM). The mixture was stirred gently at 4° C. for 16 hours. The reaction product, ALP-$SCH_2COHN$-E1-$NHCOCH_2I$, was purified by gel filtration on an AcA-44 column and shown by DTE titration to contain about 1.3 moles of iodoacetyl per mole of protein. When the reaction product (referred to as ALP-E1) was used as an indicator (500 ng protein per mL indicator) on a blank paper tab in a CKMB assay, a fluorescence rate of 146 mV/min was observed. A fluorescence rate of 9713 mV/min was observed under the same conditions using an ALP-$SCH_2COHN$-E2-$NHCOCH_2I$ preparation in which the ALP-SH polypeptide contained about 2.6 sulfhydryls per ALP molecule. Unless otherwise indicated, experiments in Examples 8–11 used an ALP preparation containing an average of one sulfhydryl group per polypeptide molecule.

Similar experiments then were carried out with other dendrimers having iodoacetyl-activated amino termini. The fluorescence response results on blank tabs for a number of iodoacetyl-activated dendrimer:ALP complexes are shown in the Table 2.

TABLE 2

Properties of ALP-Dendrimer Complexes

| Complex[e] | Fluorescence[a] 100[c] | 500[c] | Reactive Iodoacetyl Groups[d] |
|---|---|---|---|
| ALP-E1 | 35 | 146 | 1.3 |
| ALP-E2 | 31 | 265 | 2.5 |
| ALP-E3 | 169, 205[b] | 857, 972 | 5.8, 6.8 |
| ALP-E4 | 242, 185 | 1161, 903 | 8.9, 11.7 |
| ALP-E5 | 554 | 2571 | 13.7 |
| ALP-77% E5 | 1206 | 5614 | 15.2 |
| ALP-CME5 | 1798 | 8027 | 6.7 |

[a]Rates in mV/min using each complex as an indicator in a Stratus ® II instrument.
[b]Duplicate numbers indicate results from two separate experiments.
[c]Concentration of indicator used in ng polypeptide/ml solution.
[d] Number of reactive groups determined by titration of reactive groups using DTE as described in Example 4.
[e]ALP reactant contained one sulfhydryl group per polypeptide molecule.

The number of iodoacetyl groups present in the ALP:dendrimer complexes is generally lower than expected, based on the number of the amino groups present in each of the dendrimers. It is possible that non-activated, uncoupled amino group termini of a dendrimer may have reacted with neighboring iodoacetyl groups to form non-reactive cyclic structures. Although such a reaction is expected to be relatively slow, amino group termini in dendrimers may be more reactive. In addition, iodoacetyl groups incorporated into dendrimers may be more reactive than iodoacetyl groups incorporated into other types of molecules.

The specific enzyme activity was tested for the above dendrimer-polypeptide complexes using para-nitrophenol phosphate. The activity, expressed as units/mg protein, was found to be almost identical for all of the tested derivatives. This result indicates that the dendrimer generation to which ALP was coupled did not have a detrimental effect upon the enzymatic activity of ALP.

EXAMPLE 8

Coupling of Fab' to ALP-Iodoacetyl-Dendrimers

Fab' was coupled to each of the ALP:dendrimer complexes of Example 7 by incubating a reaction mixture containing about 5 mg/mL total protein in 100 mM phosphate-1.0 mM $MgCl_2$, pH 7.6. This mixture contained 1.5 to 1.9 mg of Fab' for each mg of the ALP:dendrimer complex. This ratio represents a >5-fold molar excess of Fab over the amount of ALP:dendrimer complex. After incubation at 4° C. for 24–60 hours any free sulfhydryls were quenched by the addition of N-Ethylmaleimide (NEM) as described in Example 5. After purifying the products as described in Example 9, the dendrimer:two polypeptide complexes were used as indicators in a CKMB assay as described in Example 3. The results are shown in Table 3.

TABLE 3

Fluorescence Response of ALP-$E_x$-Fab' Complexes

| | Fluorescence Response (mV/min) Calibrator[a] | | | |
|---|---|---|---|---|
| Indicator | A | B | F | Protein Conc. (ng/ml) |
| CXMB-133[b] | 107 | 317 | 7972 | |
| ALP-E1-Fab' | 124 | 329 | 7764 | 532 |
| ALP-E2-Fab' | 132 | 393 | 7910 | 618 |
| CXMB-136 | 99 | 409 | 8910 | 597 |
| ALP-E3-Fab' | 86 | 358 | 8314 | 444 |
| ALP-E4-Fab' | 187 | 486 | 9479 | 578 |
| ALP-E5-Fab' | 202 | 410 | 6721 | 9260 |

[a]Calibrators A, B and F contained 0.0, 3.9 and 131.6 ng of CKMB/mL, respectively.
[b]CXMB-133 and CXMB-136 are indicators used in Stratus ® II CKMB assay kits, comprising ALP directly coupled via SIAB to Fab'.

The results show that the fluorescence rates using an indicator composition comprising two polypeptides sequentially coupled to a dendrimer are similar to the rates for directly coupled ALP-Fab' conjugates currently used as indicators in a specific binding assay. The results further indicate that ethylenediamine core dendrimers, between generations 1 to 5, can be effectively used to sequentially couple two different proteins and form two polypeptide:dendrimer complexes in which the native biological activity of each polypeptide remains substantially the same as the activity of unconjugated polypeptide.

EXAMPLE 9

Column Profiles of Polypeptide-Dendrimer Complexes

The ALP-$E_x$-Fab' derivatives described in Example 8 were passed over an AcA-34 column (1.6 cm by 100 cm diameter) using a buffer containing 10 mM Tris, 100 mM NaCl, 1.0 mM $MgCl_2$, 0.1 mM $ZnSO_4$ and 0.1% sodium azide, pH 7.00. Higher molecular weight species elute in the earlier fractions under these conditions. Fractions (2 ml) were collected and the absorbance at 280 nanometers ($A_{280}$) was measured for each fraction. FIGS. 1 to 5 show the column profiles of the complexes formed using first to fifth generation ethylenediamine dendrimers, respectively. Arrows in each figure indicate fractions of the eluted material that were pooled for testing in a Stratus assay as described in Example 8.

Figure 2:
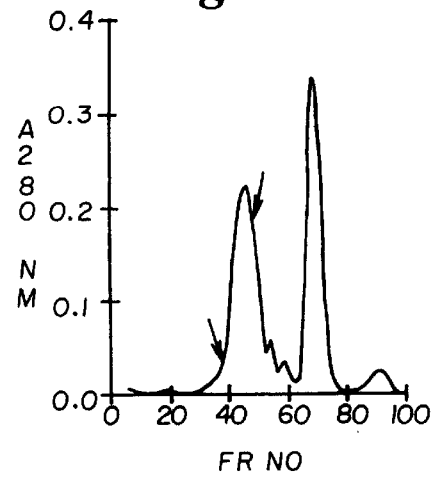
FIG. 2 shows the $A_{280}$ of column fractions of an ALP-E2-Fab' polypeptide:dendrimer complex eluted from an Ultrogel AcA-34 column.
Figure 3:
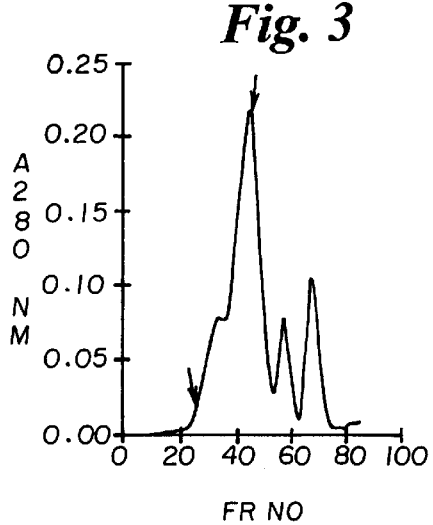
FIG. 3 shows the $A_{280}$ of column fractions of an ALP-E3-Fab' polypeptide:dendrimer complex eluted from an Ultrogel AcA-34 column.
Figure 4:
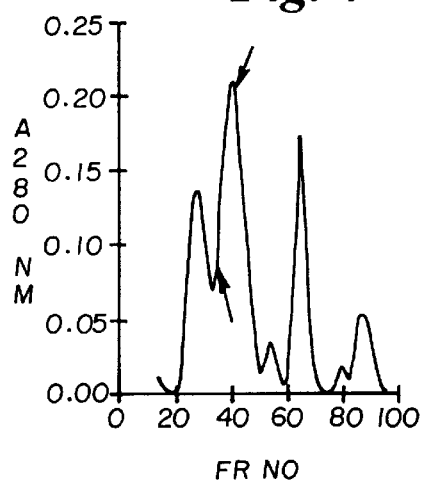
FIG. 4 shows the $A_{280}$ of column fractions of an ALP-E4-Fab' polypeptide:dendrimer complex eluted from an Ultrogel AcA-34 column.
Figure 5:
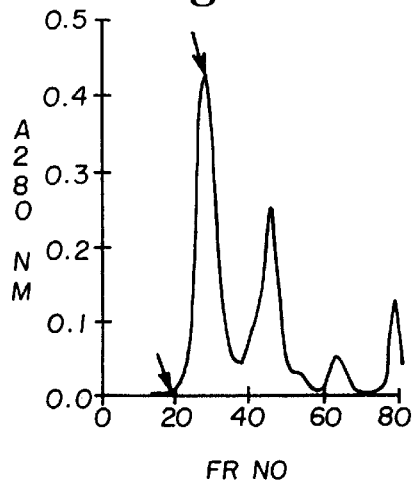
FIG. 5 shows the $A_{280}$ of column fractions of an ALP-E5-Fab' polypeptide:dendrimer complex eluted from an Ultrogel AcA-34 column.

Polypeptide-dendrimer complexes using first or second generation dendrimers appeared to be more homogeneous than the other dendrimer complexes (FIGS. 1 and 2). The column profile of ALP-E3-FAB' (FIG. 3) was almost identical to that of an ALP-Fab' complex directly conjugated by SIAB chemistry (not shown). In both cases, a high molecular weight shoulder at about fraction 32 precedes the main conjugate peak at about fraction 43.

E4 and E5 polypeptide-dendrimer complexes produced higher molecular weight species than did E1–E3 complexes. At essentially the same protein concentration, fractions of the first peak in the ALP-E4-FAB' profile (fractions 23 to 29, FIG. 4) showed about half the activity in a Stratus® CKMB assay compared to the fractions of the main peak (fractions 33 to 40, FIG. 4). The results in Table 3 represent activity of the pool from the main peak fraction. The ALP-E5-Fab' complex used in Table 3 was collected from fractions 20 to 28 (FIG. 5); this complex required a much larger amount of protein in order to give fluorescence response readings in a Stratus® assay compared to the amount of protein required by the other complexes (Table 3).

ALP-E3-Fab' complex was also purified by hydrophobic interaction chromatography on an Octyl-Sepharose column (0.8×6 cm). In hydrophobic interaction chromatography, the more hydrophobic polypeptide/dendrimer species in the reaction product are eluted in n-propanol/triethanolamine buffer. The effective protein concentration of the fractions from this column are shown in Table 4.

TABLE 4

Effective Protein Concentration[c]
of Octyl-Sepharose Column Fractions

| Complex | Column Fraction | |
|---|---|---|
| | TEA | TEA-10% PROPANOL |
| ALP-SIAB-Fab'[a] | 319[b] | 158 |
| ALP-E3-Fab' | 560 | 386 |

[a]ALP directly coupled to Fab' via an SIAB group.
[b]Effective protein concentration in ng/ml.
[c]The amount of protein/mL required to generate a response for calibrator F comparable to that generated by a commercial sample e.g. CXMB-136 in Table 3.

The more hydrophobic species of the directly coupled conjugate are effective at almost half the protein concentration compared to the less hydrophobic species. These results suggest that the proportion of the ALP and Fab' polypeptide constituents are different in ALP-SIAB-Fab' compared to ALP-E3-Fab'. The relatively small differences in the effective protein concentration of ALP-E3-Fab' before and after purification over octyl-Sepharose® suggests there are similar proportions of the two protein constituents in the complex.

EXAMPLE 10

Coupling of ALP-SH to Fab'-Dendrimer

Fab' was coupled to NIA-activated E2 by a procedure similar to that described in Example 4, except that an Fab' solution (2.6 mg/ml in pH 6.0 buffer) was used for coupling. The reaction product was Fab'-SCH$_2$COHN-E2-NHCOCH$_2$I (Fab'-E2). Fab'-E2 contained 2.5 moles of reactive iodoacetyl groups per mole of protein.

ALP-SH was then coupled to Fab'-E2 by incubating a 1.1 ml mixture of ALP-SH (2.8 mg) with 6.6 mg Fab'-E2 as described in Example 7. The reaction product (termed Fab'-E2-ALP) was purified by gel filtration on AcA-34.

The Fab'-E2-ALP product was purified over an AcA-34 column as described in Example 9. Fractions of 2 ml were collected and the A$_{280}$ of each fraction was measured. Based on the A$_{280}$ data, there was a relatively broad column profile. Different column fractions were pooled into 2 groups and the polypeptide-dendrimer complex in each pool was used as an indicator in a Stratus® CKMB assay as described in Example 3. The fluorescence response of each of the complexes is shown in Table 5.

TABLE 5

Fluorescence response of Fab'-E2-ALP Complexes
Fluorescence Response (mV/min)

| | Cal A | Cal B | Cal F |
|---|---|---|---|
| PoolA(#40–47[a]) | 519 | 538 | 1887 |
| PoolB(#49–51) | 130 | 193 | 2824 |

[a]Column fraction number.

EXAMPLE 11

Ratio of ALP to Fab' in Polypeptide-Dendrimer Complexes

The relative proportions of ALP and Fab' were determined in conjugates prepared by direct coupling through an SIAB group and complexes prepared by sequential coupling to a dendrimer. For this purpose, Fluorescein and BODIPY (Molecular Probes, Eugene, Oreg.), two fluorescent labels having different spectral characteristics, were used to label ALP and F(ab')$_2$, respectively, under mild reaction conditions known in the art. Fluorescein-containing species absorb at 495 nm and emit at 520 nm whereas BODIPY-containing species absorb at 580 nm and emit at 590 nm. The immunological activity of Fab' and the enzymatic activity of ALP were not affected by this treatment. The labeled proteins then were used to prepare ALP-E2-Fab' as described in Example 8 and an ALP-SIAB-Fab' directly coupled conjugate.

The product of each reaction was applied to an AcA-34 column and eluted with Tris buffer (Example 9). Column fractions containing polypeptide-dendrimer complex or directly coupled conjugate were collected and pooled.

Each pool then was used as an indicator in a CKMB assay as described in Example 3. Those pooled ALP-SIAB-Fab' fractions that were effective as indicators showed a range of polypeptide-dendrimer molecular weights from about 180,000 daltons to about 600,000 daltons, while those pooled ALP-E2-Fab' fractions that were effective as indicators showed molecular weights ranging from about 160,000 daltons to about 440,000 daltons.

The fluorescence originating from ALP and Fab' in each of the pools was measured in a fluorometer by setting appropriate wave lengths for excitation and emission. These measurements suggested that the ALP-SIAB-Fab' complex had a 1:6 ratio of ALP:Fab' whereas the ALP-E2-Fab' complex had a 1:3 ratio of ALP:Fab'. A higher amount of ALP per Fab' in ALP-E2-Fab' may provide an amplification of the fluorescence signal compared to ALP-SIAB-Fab'.

EXAMPLE 12

Sequential Coupling of Polypeptides to Half-Generation Dendrimers

This example teaches that a half-generation carboxyl-terminated dendrimer can be sequentially coupled to two different polypeptides.

A solution of the half-generation ethylenediamine core dendrimer (G1½-COOH), free acid (34 mg; 16 µM), in 0.5 mL of 80% aqueous DMF was mixed with 1-Ethyl-3-(3-dimethylaminopropyl)carbodiimide hydrochloride (390 mg; 2 mM; EDC) and N-hydroxysuccinimide (230 mg; 2 mM). After stirring at ambient temperature for 5 hours or for 16 hours at 4° C., the reaction mixture was mixed with 5 mL ethyl acetate. A semi-solid material that separated out was macerated with isopropanol (3×5 mL). A white fluffy solid was obtained after centrifugation (1000 rpm for 5 min) of the last isopropanol wash. The residue was dissolved in 0.5 mL water and N-hydroxysuccinimidyl ester concentration was determined by measuring the change in $A_{260}$ on addition of a 1% ethylenediamine solution to a small aliquot of the product diluted in 100 mM phosphate, pH 7.0. The reaction product was an activated half-generation dendrimer containing N-hydroxysuccinimidyl ester groups on substantially all of the dendrimer termini. A sixth half-generation ethylenediamine dendrimer solution (G(5½)-COOH) was incubated with NHS and EDC under the same conditions as described above.

Within 1 hour after preparation of the active ester solution in water, a 200–500 fold molar excess of aqueous solution of each activated ester dendrimer was reacted with ALP (3.4 mg/ml) at pH 7.0 in a refrigerator for 16 hours, to form the polypeptide-dendrimer complexes ALP-G(1½) and ALP-G (5½). Epsilon amino groups of lysine residues of ALP serve as the reactive moieties under these conditions.

The coupling efficiency of each reaction was estimated by incubating an aliquot of the ALP/activated dendrimer mixture with an excess of ethylenediamine for 16 hours at 4° C. In addition, the ALP/G(1½)-COOH activated dendrimer mixture was incubated with 2-aminoethanethiol at pH 8.0. The number of amino or thiol groups (from ethylenediamine or 2-aminoethanethiol, respectively) incorporated into ALP-G(1½) or ALP-G(5½) was determined by titration with fluorescamine or dithiodipyridine (Example 4). Aminated and thiolated ALP/dendrimer complexes were used as indicators on a blank paper tab as described in Example 6. The results of these experiments are shown in Table 6.

TABLE 6

Number of Incorporated Reactive Groups and Fluorescence Response of ALP-Half Generation Dendrimer Complexes

| Complex | NH$_2$ Groups/ Dendrimer | SH Groups/ Dendrimer | Fluorescence Response (mV/min)[a] |
|---|---|---|---|
| ALP | 44[b] | --[d] | 77 |
| ALP-G(1 1/2)-NH2 | 127 | -- | 8,004 |
| ALP-G(1 1/2)-SH | -- | 43 | 6,454 |
| ALP-G(5 1/2)-NH2 | 547 | -- | >50,000[c] |

[a]250 ng protein/ml indicator solution on blank paper tabs in a Stratus ® II
[b]Expected value is 53, based on M. Fosset, et al., Intestinal Alkaline Phosphatase: Physical properties and quaternary structure. Biochemistry:13 pp 1783–1788 (1974).
[c]Fluorescence response was greater than the maximum reading on the Stratus ® II instrument.
[d]-- = Not applicable.

The high level of non-specific binding (as shown by the fluorescence response data) indicates that there were a large number of uncoupled dendrimer termini remained in the ALP-dendrimer complexes.

ALP3 (ALP modified by periodate treatment as in Example 5) was incubated for 30 minutes as described above, using NHS-activated G(1½)-COOH dendrimer at molar ratios of 25 20:1, 100:1, and 500:1 dendrimer:ALP3. Coupling efficiency in each reaction was tested by incubating the ALP-dendrimer reaction product with 2-aminoethanethiol and determining the number of incorporated SH groups as described above. Each thiolated product was then used as an indicator on a blank paper tab in a CKMB assay and the fluorescence response was recorded. The results are shown in Table 7 below. The data indicate that as the molar challenge ratio of activated dendrimer:ALP increases, the number of incorporated SH groups increases as well as the level of non-specific binding.

TABLE 7

| Challenge ratio[a] | SH Groups/ Dendrimer[b] | Non-specific binding[c] (mV/Min) |
|---|---|---|
| 0 | 0 | 77 |
| 20 | 1.4 | 77 |
| 100 | 3.0 | 734 |
| 500 | 5.3 | 4,756 |

[a]Ratio of activated dendrimer: ALP (mole/mole) in reaction mix.
[b]Number of 2-aminoethanethiol SH groups incorporated/dendrimer determined by titration with dithiodipyridine.
[c]Fluorescence response using 250 ng of complex (protein basis)/ml indicator.

ALP3 was reacted as described above with NHS-activated G(1½)-COOH dendrimer at a challenge ratio of 50:1 activated dendrimer:ALP3. The ALP:dendrimer product was then reacted as described above with 2-aminoethanethiol. The resulting product, ALP-G(1½)-SH, contained 2.6 reactive sulfhydryls.

Fab' was activated with 1,4-butanediol diglycidyl ether (BDE), a homobifunctional cross-linker by mixing 0.16 ml of BDE (97 mM) with Fab' (0.9 mg/ml, 50 $\mu$M) and incubating at 4° C., for 24 hours in 100 mM phosphate, 5.0 mM EDTA, pH 6.0. The reaction product was shown to contain 0.5 moles of epoxide reactive moieties per mole of protein. The epoxy groups were incorporated on the sulfhydryl groups in the Fab' hinge region. ALP-G(1½)-SH and Fab'-epoxide were then coupled for 24 hours as described in Example 7. The ALP-G(1½)-Fab' polypeptide-dendrimer complex was used as an indicator in a CKMB assay as described in Example 3. The fluorescence response data are shown in Table 8.

TABLE 8

ALP-G(1 1/2)-Fab' as Indicator in CKMB Assay

| | Fluorescence Response (mV/min) | |
|---|---|---|
| | Cal A[a] | Cal F |
| CXMB-136 | 113 | 7,696 |
| ALP-G(1 1/2)-Fab' | 8,053 | 10,623 |

[a]Calibrator A is 0.0 ng/mL; Calibrator F is 131.6 ng/mL

EXAMPLE 13

Sequential Coupling of CHO- and SH-Polypeptides to COOH- and COCH$_2$Br-Termini

The free acid form of G(1½)-COOH (20 mg, 9.2 $\mu$M) dissolved in 1.0 mL of water/dioxan/DMF (1:2:2 v/v) was activated with N, N, N',N'-tetramethyl(succinimido) uronium tetrafluoroborate (TSTU) (69 mg, 230 gM) in the presence of N, N-diisopropylethylamine (89 mg, 690 AM, DPA). After one hour at ambient temperature, the volatile organics were removed under reduced pressure and a solid residue obtained was washed with ethyl acetate (3×5 mL). The ethyl acetate insoluble material was dried in vacuo and dissolved in 0.5 mL water. The concentration of active ester in the aqueous solution was determined by titration with ethylenediamine as described in Example 12; the data confirmed that substantially all of the dendrimer termini had been esterified with N-hydroxysuccinimidyl groups.

ALP3 was reacted with NHS-activated G(1½) at pH 7.0 for minutes in an ice bath as described in Example 12. The reaction mixture then was incubated with 1.5 volumes of 0.2 M hexamethylenediamine (HMD) at pH 9.0 for 2 hours, which incorporated reactive amino groups at dendrimer termini that had not been coupled to ALP.

The product was separated from non-protein impurities by ultrafiltration using pH 7.0 phosphate buffer and the number of amino groups estimated by titration with fluorescamine. The titration data showed that there were about 31 amino groups. Unreacted ALP3 is expected to have about 55 amino groups and unreacted NHS-activated G(1½) is expected to have about 12 amino group termini. The difference between the observed number of reactive amino groups (31) and the number expected in the presence of an equimolar ALP-dendrimer coupling (66) suggested that ALP3 molecules had been coupled to NHS-activated termini on G(1½)-COOH dendrimers. However, it is unlikely that substantially all of the NHS-activated dendrimer termini were coupled to an ALP molecule.

Most of the difference between the observed and expected number of reactive amino groups in the ALP-dendrimer complex likely is due to other reasons. One possible explanation, formation of an $(ALP)_n$-G(1½) complex having greater than about 2 ALP3 molecules per dendrimer was ruled out from a size exclusion column profile of the polypeptide-dendrimer complex. Uncoupled NHS-activated carboxyl termini in ALP-G(1½) may decompose to a form that does not react with HMD, or both amino groups of HMD may each react with an NHS-activated terminus. The titration calculations assume that only one amino group of HMD is reactive; if both HMD amino groups are reactive, the calculations underestimate the actual number of NHS termini remaining uncoupled to an ALP molecule.

A heterobifunctional cross-linking agent, 6-bromoacetamido-hexylamine ($BrCH_2CONH(CH_2)_6NH_2$; BAHA), was synthesized as the trifluoroacetate salt. A solution of N-hydroxysuccinimidyl bromoacetate (3.5 g/35 mL THF) was mixed with a solution of the free base prepared from N-Boc-1,6-diaminohexane hydrochloride (3.5 gm/20 mL methanol). After two hours at ambient temperature, the methanol-THF solution was evaporated to dryness on a rotary evaporator. Without purification, the white residue obtained was dissolved in 50 mL dichloromethane and 30 mL trifluoroacetic acid. The resulting clear solution was stirred at ambient temperature for two hours. The reaction mixture was evaporated to dryness on a rotary evaporator using a bath at 30° C. The white oil obtained after evaporation was crystallized from isopropanol to give 0.75 g of a white crystalline product, mp 121° C. (BAHA).

ALP3 was reacted separately with NHS-activated G(1½)-COOH and G(2½)-COOH (activated using TSTU as described above). The crude reaction mixtures (1.1 mL) were each mixed with a solution of BAHA (20 mg/0.4 mL isopropanol) and incubated at 4° C. for 16 hours. Non-protein components were removed by ultrafiltration using 100 mM phosphate, 1.0 mM $MgCl_2$, pH 7.0.

The resulting ALP-G(1½) and ALP-G(2½) complexes were titrated with 2-aminoethanethiol as described in Example 4 except that 2-aminoethanethiol was used in place of DTE. The titration results indicated that 3.9 and 4.8 reactive bromoacetamido groups, respectively, had been incorporated onto dendrimer termini uncoupled to ALP. The number of bromoacetamido groups expected if all uncoupled termini had reacted with BAHA was about 11 for ALP-G(1½) and 23 for ALP-G(2½), assuming an equimolar coupling of ALP with G(1½)-COOH and with G(2½)-COOH. ALP-G(4½)-$COCH_2Br$ (containing five 2-aminoethanethiol-reactive groups per mole of the protein) was prepared as described for ALP-G(1½)-$COCH_2Br$. The fluorescence response on blank paper tabs of ALP-G(1½), ALP-G(2½) and ALP-G(4½) indicated that these three complexes had fluorescence response rates of ≦100 mV/min. In contrast, the non-specific binding of full generation amino-terminated dendrimer-ALP complexes increased as the generation number increased (Table 3).

ALP-G(½)-$COCH_2Br$ and ALP-G(4½)-$COCH_2Br$ were reacted with Fab' for 24 hours at pH 7.6 as described in Example 8 for ALP-Iodoacetyl Dendrimer complexes. The polypeptide-dendrimer complexes ALP-G(1½)-Fab' and ALP-G(4½)-Fab' were evaluated as indicators in a specific binding assay as described in Example 3. The results are shown in Table 9.

TABLE 9

| Fluorescence Response of Half Generation Dendrimer Complexes | | | |
|---|---|---|---|
| Indicator | Cal A | Cal B | Cal F |
| CXMB-139[a] | 104 | 328 | 7698 |
| ALP-G(1 1/2)-Fab'[b] | 48 | 320 | 7083 |
| ALP-G(4 1/2)-Fab'[c] | 86 | 356 | 8454 |

[a]590 ng protein/ml indicator.
[b]740 ng protein/ml indicator.
[c]434 ng protein/ml indicator.

The performance of these complexes as indicators in a specific binding assay is similar to that of a directly conjugated indicator (CXMB-139) currently used for the same type of assay. Furthermore, the amount of protein applied to the tab for ALP-G(4½)-Fab' was about 25% less than the amount required for CXMB-139.

To the extent not already indicated, it will be understood by those of ordinary skill in the art that any one of the various specific embodiments herein described and illustrated may be further modified to incorporate features shown in other of the specific embodiments. The foregoing detailed description has been provided for a better understanding of the invention only and no unnecessary limitation should be understood therefrom as some modifications will be apparent to those skilled in the art without deviating from the spirit and scope of the appended claims.

What is claimed is:

1. A dendrimer-polypeptide complex comprising a dendrimer having a plurality of termini, said dendrimer coupled via at least one of said termini to a first polypeptide and via at least a different one of said termini to a second polypeptide, said first and second polypeptides of said complex exhibiting first and second defined biological activities, respectively, wherein one of said polypeptides is an enzyme.

2. The composition of claim 1, wherein substantially all of said termini that are not coupled to said polypeptides are blocked.

3. The composition of claim 1, wherein said dendrimer is selected from the group consisting of a first, a second, a third, a fourth and a fifth generation ethylenediamine core dendrimer.

4. The composition of claim 1, wherein said dendrimer is selected from the group consisting of a first, a second, a third, a fourth and a fifth half-generation ethylenediamine core dendrimer.

5. The composition of claim 1, wherein said enzyme forms a fluorescent, calorimetric, chemiluminescent, phosphorescent, radiometric or hybridized product.

6. The composition of claim 5, wherein said enzyme is selected from the group consisting of alkaline phosphatase, β-galactosidase, glucose oxidase, peroxidase, urease, catalase, adenosine deaminase, glycosidase, protease, esterase, DNase, RNase and acetylcholinesterase.

7. The composition of claim 1, wherein one of said defined biological activities comprises specific binding to an analyte, or a receptor for said analyte.

8. The composition of claim 7, wherein said polypeptide exhibiting said specific binding biological activity is selected from the group consisting of an antibody or antibody fragment having binding specificity for creatine kinase isozyme MB, carbonic anyhydrase 3, troponin I, myoglobin, thyroid stimulating hormone, follicle stimulating hormone, luteinizing hormone and ferritin.

9. The composition of claim 1, wherein said first polypeptide is an enzyme and said second defined biological activity comprises specific binding to an analyte, or receptor for said analyte.

10. A dendrimer-polypeptide complex comprising a dendrimer coupled to a polypeptide exhibiting a defined biological activity wherein said polypeptide is an enzyme.

11. The composition of claim 10, said dendrimer having at least one activated terminus effective for subsequently coupling a second polypeptide possessing a second defined biological activity thereto, wherein said polypeptides exhibit said respective defined biological activities following said subsequent coupling.

12. The composition of claim 10, wherein said enzyme forms a fluorescent, calorimetric, chemiluminescent, phosphorescent, radiometric or hybridized product.

13. The composition of claim 10, wherein said enzyme is selected from the group consisting of alkaline phosphatase, β-galactosidase, glucose oxidase, peroxidase, urease, catalase, adenosine deaminase, glycosidase, protease, esterase, DNase, RNase and acetylcholinesterase.

14. A method of making a dendrimer/polypeptide complex, comprising the steps of:
   a) providing a dendrimer comprising a plurality of activated termini;
   b) providing a first polypeptide having at least one reactive moiety, said first polypeptide possessing a first defined biological activity; and
   c) coupling said first polypeptide via said reactive moiety to one of said activated dendrimer termini to form a dendrimer/polypeptide complex exhibiting said first defined biological activity, said complex effective for subsequently coupling a second polypeptide possessing a second defined biological activity to another of said dendrimer termini, wherein said first and second polypeptides exhibit said respective defined biological activities following said subsequent coupling.

15. The method of claim 14, wherein said dendrimer is selected from the group consisting of a first, a second, a third, a fourth and a fifth generation ethylenediamine core dendrimer.

16. The method of claim 14, wherein said reactive moiety of said first polypeptide comprises a sulfhydryl group and said plurality of activated termini comprise a plurality of iodoacetyl groups.

17. The method of claim 14, wherein said dendrimer is selected from the group consisting of a first, a second, a third, a fourth and a fifth half-generation ethylenediamine core dendrimer.

18. The method of claim 14, wherein said reactive moiety of said first polypeptide comprises an amino group and said plurality of activated termini comprise a plurality of N-hydroxysuccinimidyl groups.

19. The method of claim 14, further comprising the steps of:
   a) providing a second polypeptide having at least one reactive moiety, said second polypeptide possessing a second defined biological activity;
   b) coupling said second polypeptide reactive moiety to one of said activated termini to form a dendrimer:two-polypeptide complex, said first and second polypeptides of said complex exhibiting said first and second defined biological activities, respectively.

20. The method of claim 19, wherein said first polypeptide reactive moiety comprises a sulfhydryl group, second polypeptide reactive moiety comprises a sulfhydryl group and said plurality of activated termini are selected from the group consisting of a plurality of iodoacetyl, bromoacetyl, chloroacetyl, epoxy and maleimidyl groups.

21. The method of claim 14, wherein at least one of said activated termini in said complex is uncoupled, said method further comprising the steps of:
   a) activating said at least one uncoupled terminus of said dendrimer/polypeptide complex with a second activating group to form a second activated terminus;
   b) providing a second polypeptide having a reactive moiety, said second polypeptide possessing a second defined biological activity; and
   c) coupling said second polypeptide reactive moiety to said second activated terminus to form a dendrimer:two-polypeptide complex, said first and second polypeptides of said complex exhibiting said first and second defined biological activities, respectively.

22. The method of claim 21, wherein said first polypeptide reactive moiety comprises an amino group, said second polypeptide reactive moiety comprises a sulfhydryl group, said plurality of activated termini comprise a plurality of N-hydroxysuccinimidyl groups and said second activated terminus is selected from the group consisting of a bromoacetyl, iodoacetyl, chloroacetyl, epoxy and maleimidyl group.

23. The method of claim 14, wherein said first polypeptide or said second polypeptide is an enzyme.

24. A method for conducting a specific binding assay to determine the concentration or presence of an analyte in a sample, comprising the steps of:
   a) immobilizing an effective amount of a specific binding assay reagent with specificity for said analyte, or for a receptor of said analyte, to a solid phase;
   b) applying said sample under binding conditions to said solid phase;
   c) applying an indicator comprising a dendrimer having a plurality of termini, said dendrimer coupled via at least a first of said termini to a first polypeptide and via at least a second of said termini to a second polypeptide, one of said polypeptides comprising a label and the other of said polypeptides comprising a specific binding receptor for said analyte, or for a receptor of said analyte;
   d) determining the amount of said dendrimer-polypeptide indicator bound to said solid phase; and
   e) correlating said amount of said indicator with the concentration or presence of said analyte, or receptor of said analyte, in said sample.

25. The method of claim 24, wherein substantially all of said termini that are not coupled to said polypeptides are blocked.

26. A method for conducting a specific binding assay to determine the concentration or presence of an analyte in a sample, comprising the steps of:

a) providing a reagent solution comprising an effective amount of a specific binding assay reagent with specificity for said analyte, or for a receptor of said analyte;

b) adding said sample under specific binding conditions to said reagent solution to form an assay solution;

c) adding an effective amount of said assay solution to a solid phase under conditions effecting immobilization of said reagent on said solid phase;

d) applying to said solid phase an indicator comprising a dendrimer having a plurality of termini, said dendrimer coupled via at least a first of said termini to a first polypeptide and via at least a second of said termini to a second polypeptide, one of said polypeptides comprising a label and the other of said polypeptides comprising a specific binding receptor for said analyte, or for a receptor of said analyte;

e) determining the amount of said dendrimer-polypeptide indicator bound to said solid phase; and f) correlating said amount of said indicator with the concentration or presence of said analyte, or receptor of said analyte, in said sample.

27. The method of claim 26, wherein substantially all of said termini that are not coupled to said polypeptides are blocked.

28. A method of making a dendrimer/polypeptide complex, comprising the steps of:

a) providing a dendrimer comprising a plurality of activated termini; and b) coupling a polypeptide to said dendrimer via a reactive moiety on said polypeptide and one of said activated termini, said polypeptide exhibiting a defined biological activity wherein said polypeptide is an enzyme.

* * * * *